United States Patent
Lowe et al.

(10) Patent No.: US 7,098,321 B2
(45) Date of Patent: Aug. 29, 2006

(54) HOMOLOGOUS PEPTIDE NUCLEIC ACIDS

(75) Inventors: Gordon Lowe, Oxford (GB); Tirayut Vilaivan, Bangkok (TH)

(73) Assignee: Isis Innovation Limited, Summertown (GB)

( * ) Notice: Subject to any disclaimer, the term of this patent is extended or adjusted under 35 U.S.C. 154(b) by 120 days.

(21) Appl. No.: 10/357,589

(22) Filed: Feb. 4, 2003

(65) Prior Publication Data
US 2003/0228588 A1 Dec. 11, 2003

Related U.S. Application Data

(63) Continuation-in-part of application No. 10/161,090, filed on May 31, 2002, now abandoned.

(30) Foreign Application Priority Data

Feb. 4, 2002 (GB) .................................. 0202552.6
Jun. 27, 2002 (GB) .................................. 0214897.1

(51) Int. Cl.
C07H 21/00 (2006.01)
C07H 21/02 (2006.01)
C07H 21/04 (2006.01)
C12Q 1/68 (2006.01)

(52) U.S. Cl. .................... 536/23.1; 536/25.3; 536/26.6; 435/6

(58) Field of Classification Search ............... 536/23.1, 536/25.3, 26.6; 435/6
See application file for complete search history.

(56) References Cited

FOREIGN PATENT DOCUMENTS

WO      WO 98/16650 A1      4/1998

OTHER PUBLICATIONS

Vilaivan, Tirayut et al., "Synthesis and properties of novel pyrrolidinyl PNA carrying β-amino acid spacers," Tetrahedron Letters 42 (2001) 5533-5536.
Lin, P. Kong Thoo et al., "Synthesis and duplex stability of oligonucleotides containing cystosine-thymine analogus", Nucleic Acids Research (1989) 17, 10373-10383.
Vilaivan, Tirayut, et al., "Synthesis and Properties of Chiral Peptide Nucleic Acids with N-Aminoethyl-D-proline Backbone," Bioorg. & Med. Chem. Letters 10 (2000) 2541-2545.
Klosterman, H.J., et al., "Isolation, Charactcrization, and Synthesis of Linatine A. Vitamin", Biochemistry (1967) 6 170-177.
Lowe, Gordon, et al., "Solid-phase synthesis of novel peptide nucleic acids," J. Chem. Soc., Perkin Trans. 1 (1997) 555-560.
Thomson, Stephen A., et al. "Frnoc Mediated Synthesis of Peptide Nucleic Acids," Tetrahedron (1995) 51 6179-6194.
Nielsen, Peter E., et al., "Peptide nucleic acid (PNA). A DNA mimic with a pseudopeptide backbone," Chem. Soc. Reviews (1997) 73-78.

(Continued)

Primary Examiner—Jezia Riley
(74) Attorney, Agent, or Firm—Wolf, Greenfield & Sacks, P.C.

(57) ABSTRACT

The invention discloses compounds of the formula:

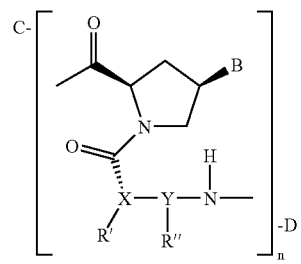

where n is 1, or 2 to 200 in which case each recurring unit can be the same or different,
B is a protected or unprotected base capable of Watson-Crick or of Hoogsteen pairing.
C is OH or OR''' where R''' is a protecting group or an activating group or a lipophilic group or an amino acid or amino amide or nucleoside,
D is H or a protecting group or a lipophilic group or an amino acyl group or nucleoside,
each of R' and R", which may be the same or different, is an alkyl or aryl group or R' and R" together represent 2 or more chain atoms necessary to complete an unsaturated or saturated ring with X and Y, said ring being optionally substituted and optionally being fused to at least one other ring,
X represents

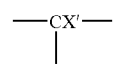

and Y represents

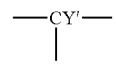

or

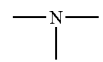

wherein Y' represents hydrogen or additionally, when R' and R" do not together complete a ring, an alkyl or aryl group, and X', when R' and R" together complete a ring, represents hydrogen or forms a bridge with another atom of the ring, or when R' and R" do not together complete a ring, represents hydrogen or an alkyl or aryl group as well as a method of analysing a polynucleotide sequence comprising incubating the sequence with a probe comprising a compound of the above invention in which n is 2 or more under suitable hybridisation conditions, and detecting the presence or absence of any hybrid formed.

26 Claims, 2 Drawing Sheets

OTHER PUBLICATIONS

Steely, et al., "CD of homopolymet DNA-RNA hybrid duplexes and triplexes containing A-T or A-U base pairs," Nucleic Acids Res. (1986) 14 10071-10090.

Tomac, et al. "Ionic Effects on the Stability and Conformation of Peptide Nucleic Acid Complexes," J. Am. Chem. Soc. (1996) 118, 5544-5522.

Marky, et al. "Calculating Thermodynamic Data for Transitions of any Molecularity from Equilibrium Melting Curves," Biopolymers, (1987) 26, 1601-1620.

Puglisi, et al., Absorbance Melting Curves of RNA, Methods in Enzymology (1989) 180, 304-325.

Cassani, et al., Oligodeoxythymidylate: Polydeoxyadenylate and oligodeoxyadenylate: Polydeoxythymidylate Interactions, Biochemistry (1969) 8, 3928-3936.

Haaima, et al., "Peptide nucleic acids (PNA) derived from N-(N-methylaminoethyl)glycine. Synthesis, hybridization and structural properties," New J. Chem., (1999) 23, 833-8440.

Lowe, et al., "Dipeptides bearing nucleobases for the synthesis of novel peptide nucleic acids," J. Chem. Soc., Perkin Trans. (1997) 1 547-554.

Lowe, et al., "Hybridization Studies with Chiral Peptide Nucleic Acids," Biogranic Chem. (1997) 25, 321-329.

Vilaivan, Tirayut et al., Synthesis and Properties of Novel peptide Nucleic Acids with Hydrophilic Serine Spacers, ScienceAsia (2001) 27, 113-120.

Figure 3 (top)

Figure 3 (bottom)

HOMOLOGOUS PEPTIDE NUCLEIC ACIDS

RELATED APPLICATIONS

This application is a continuation-in-part of U.S. patent application Ser. No. 10/161,090, filed May 31, 2002, now abandoned, the entire disclosure of which is incorporated by reference herein.

This invention relates to homologous peptide nucleic acids.

Peptide nucleic acid (PNA1) is a DNA analogue with the deoxyribose phosphate replaced by a polyamide backbone derived from N-aminoethylglycine. In spite of such a dramatic structural change, PNA shows a high affinity towards DNA and RNA in a sequence-specific fashion. It also displays unique binding properties not found in other DNA analogues, for example PNA can bind to double stranded DNA by a strand displacement mechanism. Because of its great potential as a tool in many biological applications including antisense research, analogues of PNA became an attractive research target soon after PNA was reported. Several modifications of PNA have been made in order to search for better affinity, specificity, solubility and cell membrane penetration but only limited success has been reported.

In our WO 98/16550 we describe PNAs of the formula:

where n is 1 or 2–200

B is a protected or unprotected heterocyclic base capable of Watson-Crick or of Hoogsteen pairing.

R is H, C1–C12 alkyl, C6–C12 aralkyl or C6–C12 heteroaryl which may carry one or more substituents preferably selected from hydroxyl, carboxyl, amine, amide, thiol, thioether or phenol,

X is OH or OR''' where R''' is a protecting group or an activating group or a lipophilic group or an amino acid or amino amide or nucleoside, Y is H or a protecting group or a lipophilic group or an amino acyl group or nucleoside.

When n is 1, these compounds are peptide nucleotide analogues. When n is 2 to about 30 these compounds are peptide oligonucleotide analogues and can be hybridised to ordinary oligo or polynucleotides. Typically the two strands are hybridised to one another in a 1:1 molar ratio by base-specific Watson-Crick base pairing.

We believed it should be possible to further enhance the binding of these PNAs to complementary oligonucleotides by replacing the glycine residue with an alternative spacer with an appropriate conformational rigidity. Molecular modelling suggested that if the glycine spacer is replaced by a β-amino acid in which the dihedral angle between the amino group and the carboxylic acid is close to 0°, a very favourable geometry for hybridization to complementary oligonucleotide should result.

According to the present invention, there is provided a compound of formula (2):

where n is 1, or 2 to 200, in which case each recurring unit, can be the same or different,

B is a protected or unprotected base capable of Watson-Crick or of Hoogsteen pairing, C is OH or OR''' where R''' is a protecting group or an activating group or a lipophilic group or an amino acid or amino amide or nucleoside,

D is H or a protecting group or a lipophilic group or an amino acyl group or nucleoside and R' and R'' which are the same or different, are H, $C_{1-6}$ alkyl, aryl, aryl(C1–C6)alkyl or R' and R'' together with the carbon atoms to which they are attached form a cycloalkyl ring, each of R' and R'', which may be the same or different, is an alkyl or aryl group or R' and R'' together represent 2 or more chain atoms necessary to complete an unsaturated or saturated ring with X and Y, said ring being optionally substituted and optionally being fused to at least one other ring,

X represents and Y represents or wherein Y' represents hydrogen or additionally, when R' and R'' do not together complete a ring, an alkyl or aryl group, and X', when R' and R'' together complete a ring, represents hydrogen or forms a bridge with another atom of the ring, or when R' and R'' do not together complete a ring, represents hydrogen or an alkyl or aryl group.

B is a base capable of Watson-Crick or of Hoogsteen pairing. This may be a naturally occurring nucleobase selected from A,C,G,T and U; or a base analogue that may be base specific or degenerate, e.g. by having the ability to base pair with both pyrimidines (T/C) or both purines (A/G)

or universal, by forming base pairs with each of the natural bases without discrimination. Many such base analogues are known e.g. hypoxanthene, 3-nitropyrrole, 5-nitroindole, and those cited in Nucleic Acids Research, 1989, 17, 10373–83 and all are envisaged for use in the present invention.

The stereochemistry of the compounds is believed to be important.

Any one of B, C and D may include a signal moiety, which may be for example a radioisotope, an isotope detectable by mass spectrometry or NMR, a hapten, a fluorescent group or a component of a chemiluminescent or fluorescent or chromogenic system. The signal moiety may be joined to the peptide nucleotide analogue either directly or through a linker chain of up to 30 atoms as well known in the field.

When R' and R" complete a ring within X and Y this ring typically possesses 4 to 7 atoms, i.e. 4, 5, 6 or 7 atoms. The atoms which complete the ring may all be carbon atoms although the presence of heteroatoms, for example oxygen, nitrogen and sulphur atoms, is not excluded. The ring is generally saturated.

As indicated above, the ring may be fused to one or more other rings, typically of 4 to 7 atoms, for example carbon atoms, as in a bicyclic system. Although this ring may be saturated it can also be unsaturated and typically aromatic, for example benzene.

The ring or rings may optionally be substituted, generally not ortho to the chain atoms of X and Y or to the points of fusion and preferably, therefore, meta or para. The nature of the substituents is not particularly critical.

Suitable substituents include halogen, hydroxyl, $C_1$–$C_6$ alkoxy, which is unsubstituted or substituted, $C_2$–$C_6$ alkenyl, aryl, aryloxy, heteroaryloxy, $C_1$–$C_6$ alkyl which is unsubstituted or substituted, nitro, cyano, azido, amidoxime, $C_2R^{10}$, $CON(R^{12})_2$, $OCON(R^{12})_2$, $SR^{10}$, $SOR^{11}$, $SO_2R^{11}$, $SO_2N(R^{12})_2$, $N(R^{12})_2$, $NR^{10}SO_2R_{11}$, $N(SO_2R^{11})_2$, $NR^{10}(CH_2)_n CN$, $NR^{10}COR^{11}$, $OCOR^{11}$ or $COR^{10}$ where $R^{10}$ is hydrogen, $C_1$–$C_6$ alkyl, $C_3$–$C_{10}$ cycloalkyl, benzyl or phenyl; $R^{11}$ is $C_1$–$C_6$ alkyl, $C_3$–$C_{10}$ cycloalkyl, benzyl or phenyl; each $R^{12}$, which are the same or different, is hydrogen, $C_1$–$C_6$ alkyl, cycloalkyl, benzyl or phenyl, or the two $R^{12}$ groups form, together with the nitrogen atom to which they are attached, a 5- or 6-membered saturated N-containing heterocyclic ring which may include 1 or 2 additional heteroatoms selected from O, N and S; and n is 1, 2 or 3.

R' and R" can independently represent alkyl or aryl groups, as can X' and Y' when R' and R" represent these substituents. Desirably X' and Y' and R' and R" should be so chosen so as to lock the desired conformation of the molecule which can otherwise be achieved by forming a ring with R' and R". The alkyl and aryl groups can be substituted. The nature of the substituents is not particularly critical. Generally the alkyl groups are $C_{1-6}$.

A $C_1$–$C_6$ alkyl group may be linear or branched. A $C_1$–$C_6$ alkyl group is typically a $C_1$–$C_4$ alkyl group, for example a methyl, ethyl, propyl, i-propyl, n-butyl, sec-butyl or tert-butyl group. A $C_1$–$C_6$ alkyl group which is substituted is typically substituted by one or more halogen atoms, for instance by 1, 2 or 3 halogen atoms. It may be a perhaloalkyl group, for instance trifluoromethyl.

A halogen is F, Cl, Br or I. Preferably it is F, Cl or Br.

A $C_1$–$C_6$ alkoxy group may be linear or branched. It is typically a $C_1$–$C_4$ alkoxy group, for example a methoxy, ethoxy, propoxy, i-propoxy, n-propoxy, n-butoxy, sec-butoxy or tert-butoxy group.

As used herein an aryl group is typically a $C_{6-10}$ aryl group such as phenyl or naphthyl, preferably phenyl. An aryl group may be unsubstituted or substituted at any position, with one or more substituents. Typically, it is unsubstituted or carries one or two substituents. Suitable substituents include $C_{1-4}$ alkyl, $C_{1-4}$ alkenyl, each of which may be substituted by one or more halogens, halogen, hydroxyl, cyano, $-NR_2$, nitro, oxo, $-CO_2R$, $-SOR$ and $-SO_2R$ wherein each R may be identical or different and is selected from hydrogen and $C_{1-4}$ alkyl.

As used herein a heterocyclic group is a 5- to 7-membered ring containing one or more heteroatoms selected from N, O and S. Typical examples include pyridyl, pyrazinyl, pyrimidinyl, pyridazinyl, furanyl, thienyl, pyrazolidinyl, pyrrolyl and pyrazolyl groups. A heterocyclic group may be substituted or unsubstituted at any position, with one or more substituents. Typically, a heterocyclic group is unsubstituted or substituted by one or two substituents. Suitable substituents include $C_{1-4}$ alkyl, $C_{1-4}$ alkenyl, each of which may be substituted by one or more halogens, halogen, hydroxyl, cyano, $-NR_2$, nitro, oxo, $-CO_2R$, $-SOR$ and $-SO_2R$ wherein each R may be identical or different and is selected from hydrogen and $C_{1-4}$ alkyl.

As used herein, halogen is fluorine, chlorine bromine or iodine, preferably fluorine, chlorine or bromine.

A bridge can also be formed by X' and another atom of the first or other ring. Typically this is a $-CH_2-$ or $-CH_2-CH_2-$ bridge.

Preferred rings present in the compounds of the invention include those with the following skeletons:

It is therefore preferred that Y represents and that R' and R" complete a 4, 5 or 6 membered saturated nitrogen-containing ring, especially pyrrolidine.

The present invention also provides a process for preparing the compounds of the present invention which comprises:

(i) de-protecting the heterocyclic amino group of a compound of the formula:

(a)

where R² is a protecting group, for example Dpm (diphenylmethyl) or Pfp (pentafluorophenyl), R³ is a protecting group compatible with R² for example Boc (t-butoxycarbonyl) or Fmoc (9-fluorenylmethyl formate), and B is a protected or unprotected heterocyclic base capable of Watson-Crick or Hoogsteen pairing, in particular
N₃— protected (such as by benzoyl) thymine,
N₆— protected adenine, N₄— protected cytosine, N₂—O₆— protected guanine or
N₃— protected uracil, (ii) deprotecting the compound of the formula:

(b)

where X, Y, R² and R³ are as defined above, and (iii) coupling the two deprotected compounds together. It will be appreciated that compounds of the present invention can readily be made from proline.

In another aspect the invention provides a method of converting a peptide nucleotide analogue of the invention in which n is 1 into a peptide oligonucleotide of the same formula in which n is 2–200, comprising the steps of:
(i) providing a support carrying primary amine groups,
(ii) coupling an N-protected peptide nucleotide analogue of this invention in which n is 1 to the support,
(iii) removing the N-terminal protecting group,
(iv) coupling an N-protected nucleotide analogue of this invention in which n is 1 to the thus-derivatised support,
(v) repeating steps (iii) and (iv) one or more times, and
(vi) optionally removing the resulting peptide oligonucleotide from the support.

A procedure for synthesis of the compounds is illustrated in Example 1.

Compounds carrying a hydrophilic N-aminoethylproline backbone can be readily synthesised using standard peptide chemistry (see, for example, Biorg. v Med. Chem. Letters 0(2000) 1–5). The PNA is readily soluble in aqueous solvents and exhibits strong interaction with oligoribonucleotides but not with oligodeoxyribonucleotides. Such high selectivity suggests it has potential as an antisense agent where selective targeting of mRNA would be beneficial.

The present invention also provides a pharmaceutical composition which comprises a compound of the present invention and a pharmaceutically acceptable diluent or carrier.

The compounds of the present invention have been found to be particularly useful as probes in carrying out hybridisation studies. In particular, the bases B of the probe can be selected to provide a desired sequence and can be used to probe for the presence of that target sequence in a polynucleotide sequence. It has been found that the probes of the present invention are particularly suited to distinguishing between a complementary sequence and a sequence incorporating one or more mismatches with respect to the probe. Thus, the probe can be provided for use in a method of analysing a polynucleotide sequence comprising carrying out hybridisation studies using a compound of the invention as a probe. Preferably, in accordance with this aspect of the invention, n is 5 or more, for example n is between 5 to about 200, more preferably between 5 and 30.

In accordance with this aspect of the invention, a probe of the invention is incubated with the polynucleotide sequence under suitable hybridisation conditions. The conditions are selected such that for the length of probe, and the length of polynucleotide sequence, the probe can be used to distinguish between a perfectly complementary sequence and a sequence having one or more mismatches. Typically, hybridisation may be carried out by heating the sample to about 70° C., more preferably between about 75° C. and 90° C., such as about 80° C. or 85° C., and allowing the sample to cool slowly such that the oligonucleotides hybridize to the most favoured binding site. Typically, the salt concentration is fairly low, such as less than 20 mM, such as 10 mM. The pH is preferably 7 or less, since the probes of the invention are partially protonated. Following hybridisation of the probe to the sequence under analysis, optionally, a wash step may be included to remove unbound probe from the sample.

The sequence under analysis, or the probe may be bound to a solid support. Preferably, in this embodiment, a wash step is included to remove unbound probes. Any suitable solid support may be used. Typically, where a PNA of the invention is bound to a solid support, the solid support is an insoluble polymer such as polystyrene onto which is grafted a water soluble polymer such as polyethylene glycol to cover the surface of the insoluble polymer.

Subsequently, hybrids between a probe of the invention and the polynucleotide sequence can be detected to establish whether the target sequence is perfectly complementary to the probe of the invention or incorporates a mismatch sequence. Any suitable label may be used to label and identify probes. For example, probes may be supplied with a radiolabel, flourescent label or other readily detectable label.

Any suitable means may be used to detect hybrids between a probe of the invention and the polynucleotide sequence. For example, hybridisation could be detected by detecting the change of the wavelength of the flourescent maximum and its intensity. The studies may be carried out such that the hybridisation conditions are selected such that only a perfectly complementary nucleotide sequence would hybridise to the probe, with subsequent detection of any hybrids formed. Alternatively, the $T_m$ could be monitored to deduce whether the probe is hybridised to a complimentary or mismatched nucleotide sequence. Optionally, where a mismatch sequence is hybridised, the sequence may be cut out and sequenced to establish its sequence.

Alternatively, where a solid support is used, labels could be attached to the target nucleotide sequences or the probes, whichever is not attached to the solid support. After washing, label associated with the solid support, such as the level of radioactivity could be monitored. Mass spectrometry may also be used for detection. In this embodiment, the probe is bound to a solid support. After hybridisation, the support is washed thoroughly. Subsequently, the hybrid is denatured from the probe on the solid support and detected by mass spectometry. The probes of the present invention do not act as PCR primers. Thus, these probes could also be used to prevent primers of appropriate sequence from acting as PCT primers. Thus, the PNA probes of the present invention may also be incubated with a sample incorporating other primers. Inhibition of PCR could be used to monitor for hybridisation of the PNA probe to a perfectly matched sequence.

The method may be carried out using two probes of the invention, one of which is perfectly complementary to a selected target sequence, and one of which incorporates a mismatch. Both probes are incubated with the sequence to be analysed and hybrids detected as before. The probes may be labelled with different labels, such that it may be possible to establish not only whether the sequence under analysis has the selected target sequence or not, but also whether the sequence has a selected mismatch to the selected target sequence, by virtue of bonding to the second probe. This method is particularly useful for identification of single nucleotide polymorphisms (SNP's).

In one aspect of the invention, the polynucleotide to be analysed or the probe may first be provided with a tag, such as one member of a specific binding pair. Such a tag could be used, for example, to isolate the relevant polynucleotide from the hybridisation solution, for subsequent detection of any probe bound to the polynucleotide.

A probe in accordance with the present invention preferentially binds to DNA as opposed to RNA. Accordingly, the probes of the present invention may also be used for hybridisation to DNA sequences in order to assist in isolation of such DNA sequences from mixtures of RNA and DNA.

In one embodiment of the present invention, the PNA probe may comprise a chimeric oligonucleotide incorporating a PNA of the present invention of 5 or more bases in length flanked on either or both sides by oligonucleotides having an alternative backbone. For example, the probe may have a PNA-DNA backbone. Such mixed probes could be used such that the PNA portion is selected to differentiate between a perfectly complementary sequence and a mismatched sequence. The flanking DNA sequences may then be used as primers to drive the polymerase chain reaction. Such probes may be used to obtain amplification only of those sequences which incorporate perfectly matched sequences and to facilitate a reduction in amplification of any non-mismatched sequences.

The following Examples further illustrate the present invention:

EXAMPLE 1

The following procedure is illustrative, 3b-T$_{10}$ being a compound of this invention.

Syntheses of 3a-T$_{10}$, 3b-T$_{10}$ and 3c-T$_{10}$ require the protected building blocks including Fmoc-L-aminopyrrolidine-2-carboxylic acid pentafluorophenyl ester (4a), Fmoc-D-aminopyrrolidine-2-carboxylic acid pentafluorophenyl ester (4b) (1R,2S)-2-aminocyclo-pentanecarboxylic acid pentafluorophenyl ester (4c) and Fmoc-protected PNA monomer (6). Both D- and L-aminopyrrolidine-2-carboxylic acid were synthesised from D- and L-proline via the corresponding N-nitrosoprolines as described in Biochemistry, 1967, 6, 170. Protection of D- and L-aminopyrrolidine-2-carboxylic acid with Fmoc-Cl followed by activation with pentafluorophenyl trifluoroacetate/DIEA gave pentafluorophenyl esters (4a) and (4b) respectively. (−)-Cispentain [(1R,2S)-

2-aminocyclopentanecarboxylic acid] (see J. Chem. Soc. Perkin Trans. I, 1994, 1411–1415) was similarly protected and activated to give the pentafluorophenyl ester (4c). Boc-protected thymine monomer (5) (see J. Chem. Soc. Perkin Trans I, 1997, 547–554) was converted to the activated Fmoc-protected PNA monomer (6) in four steps (Scheme 1). The PNA syntheses were performed in a stepwise fashion without pre-formation of the dipeptide building blocks. For comparison, the flexible β-alanine was also used as spacer. In this case the dipeptide building block was synthesised by selective deprotection of the N-Boc group in the thymine monomer (5) by p-toluenesulfonic acid-acetonitrile (Biochemistry loc. cit.) followed by ECD.HCl mediated coupling with commercially available Fmoc-β-alanine. The dipeptide was treated with 4 M HCl in dioxane to deprotect the diphenylmethyl ester followed by treatment with pentafluorophenyl trifluoroacetate/DIEA to give the activated dipeptide (7) in 43% overall yield (Scheme 1):

TABLE 1

ESI-MS spectra of the PNA 3a–3d

| PNA | $M_r$ found | $M_r$ calcd. |
|---|---|---|
| 3a-$T_{10}$ | 3476.25, 3515.00, 3553.75 | 3478.69 (M), 3516.76 (M − H + K), 3554.88 (M − 2H + 2K) |
| 3b-$T_{10}$ | 3478.54, 3516.70, 3539.92, 3554.69 | 3478.69 (M), 3516.79 (M − H + K), 3538.77 (M − 2H + Na + K), 3554.88 (M − 2H + 2K) |
| 3c-$T_{10}$ | 3469.08, 3492.56, 3507.13, 3531.48 and 3544.16 | 3468.82 (M); 3490.80 (M − H + Na); 3506.91 (M − H + K), 3528.89 (M − 2H + K + Na), 3545.01 (M − 2H + 2K) |

Scheme 1 i) 2.5 eq p-TsOH.H₂O/MeCN, rt
ii) Fmoc-β-Ala-OH/EDC·HCl, rt, O/N
iii) Fmoc-Cl/DIEA, rt, 2 h
iv) Hcl/dioxane, rt, 6 h
v) PfpOTfa/DIEA in DMF, rt 15 min Oligomerisation of these building blocks was performed on Novasyn TGR resin (2.5 μmol scale for PNA 3a–3c and 5 μmol scale for PNA 3d) as described in J. Chem. Soc. Perkin Trans. 1997, 555–560. Lysine amide was included at the N-termini of all PNA for comparison with previous PNA in this series. Each pentafluorophenyl activated monomer was attached to the resin using 4 equivalents of the monomer and 4 equivalents of HOAt in DMF (60 min, single coupling). Capping (Ac₂O/DIEA) was performed after each step. After removal of the N-Fmoc group by treatment with 20% piperidine in DMF, the synthesis cycle was repeated until the complete sequence of 3a-$T_{10}$, 3b-$T_{10}$, 3c-$T_{10}$ and 3d-$T_{10}$ were obtained. Quantitative monitoring of the dibenzofulvene-piperidine adduct released during Fmoc group deprotection showed that all coupling reactions proceed fairly efficiently (average coupling efficiency per cycle: 3a-$T_{10}$ 98.0, 3b-$T_{10}$ 99.2%, 3c-$T_{10}$ 99.8%, 3d-$T_{10}$ 96.4%). The crude PNAs were released from the resin by treatment with trifluroacetic acid without prior deprotection of the Fmoc group in order to use it as a purification handle (see Tetrahedron, 1995, 51, 6179–6194). After purification by reverse phase HPLC, the Fmoc-ON PNAs were treated with 20% piperidine in DMF to give the fully deprotected PNAs which were characterised by ESI-mass spectrometry (Table 1).

TABLE 1-continued

ESI-MS spectra of the PNA 3a–3d

| PNA | $M_r$ found | $M_r$ calcd. |
|---|---|---|
| 3d-$T_{10}$ | 3067.00, 3089.13 and 3104.17 | 3068.16 (M); 3090.14 (M − H + Na); 3106.25 (M − H + K) |

Figure 1:
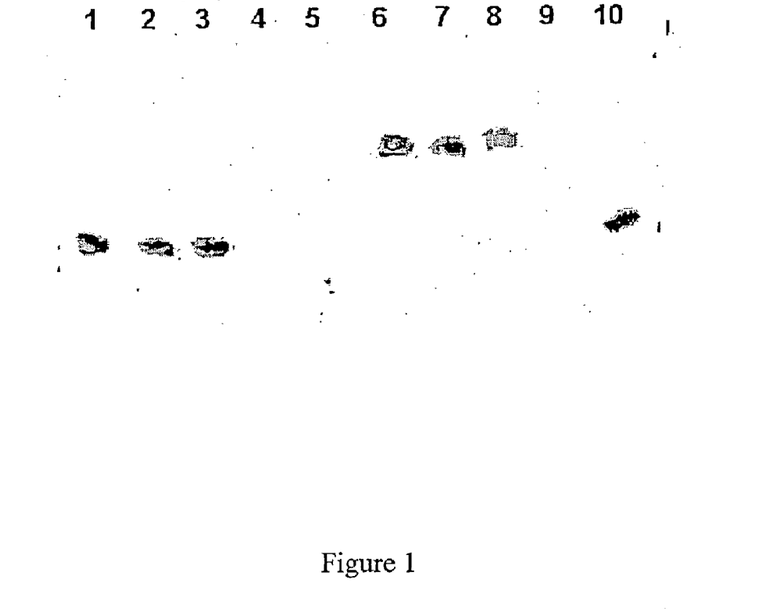
FIG. 1: Gel hybridisation experiment. Lane 1: FdA$_{10}$+3d-T$_{10}$; Lane 2: FdA$_{10}$+3c-T$_{10}$; Lane 3: FdA$_{10}$+3a-T$_{10}$; Lane 4-5: not used; Lane 6-8: FdA$_{10}$+3b-T$_{10}$1:1, 1:2, 1:5; Lane 9: not used; Lane 10: FdA$_{10}$ (negative control); Conditions: The electrophoresis experiments were carried out on 15% polyacrylamide gel in 90 mM TBE buffer pH 8.3 at a constant DC voltage of 100 V.
Figure 2:
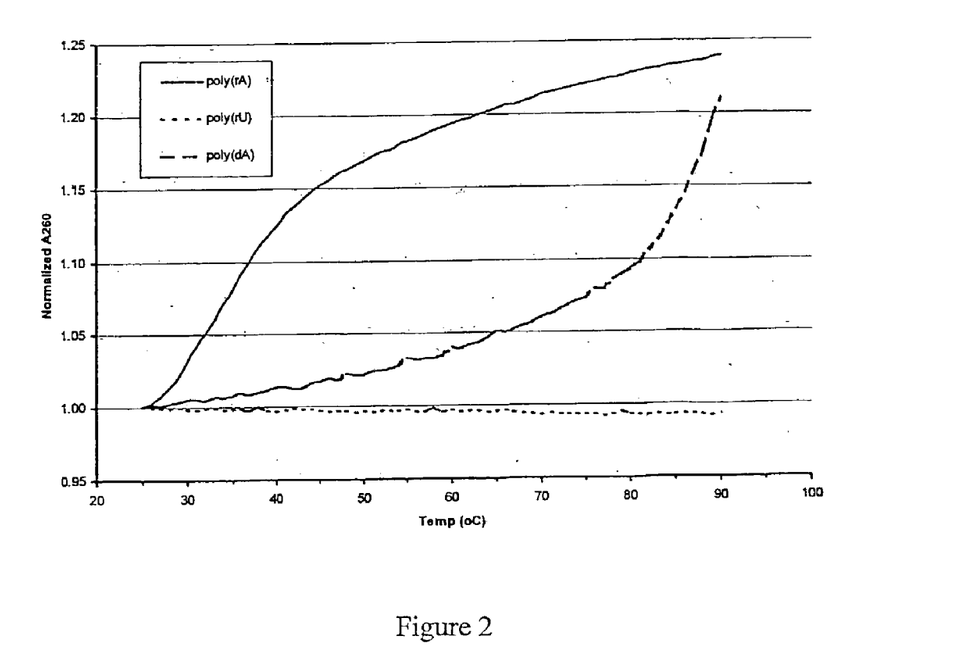
FIG. 2: Melting curve of a 1:1 mixture between 3b and poly(rA), poly(rU) and poly(dA). Conditions as set out in the text.

Preliminary binding studies of the four novel β-PNA to oligodeoxyribonucleotide were carried out by polyacrylamide gel binding shift technique using fluorescently labelled $(DA)_{10}$ "$(FdA_{10})$" as a probe. After a brief incubation of 1:1 mixtures of the PNA and DNA at 20° C., the samples were electrophoresed in 15% polyacrylamide gel at the same temperature. Only PNA 3b-$T_{10}$ bearing a D aminopyrrolidinecarboxylic acid spacer showed positive results as evidenced by the presence of a new slow-moving fluorescent band and the disappearance of the fluorescent $(DA)_{10}$ band see FIG. 1. Furthermore, only 3b-$T_{10}$ showed an observable melting with poly(dA) with a $T_m$ value greater than 80° C. at 150 mM NaCl and pH 7 (FIG. 2).

The binding of β-PNA to their complementary oligonucleotide is remarkable since this appeared to violate Nielsen's "6+3" principle (Chem. Soc. Rev. 1997, 73–78). It is also of interest to note that only PNA 3b-$T_{10}$ bearing D-aminopyrrolidine-2-carboxylic acid spacer gave positive results while the PNA bearing L-aminopyrrolidine-2-carboxylic acid spacer did not. The sterochemistry of the building blocks has great influence on the conformation of the oligomers which may account for the results. Incidentally, PNA 3c bearing (1R,2S)-2-aminocyclopentane carboxylic acid with an L-configuration at the a-carbon of the spacer also did not show evidence of binding to $(dA)_{10}$. PNA 3d bearing a relatively flexible β-alanine spacer, should, in principle, be able to adopt any conformation required for binding to its complementary DNA. The lack of binding to DNA in this case may arise from the fact that entropy loss during the binding process would be high.

EXAMPLE 2

As part of our continuing investigation into conformationally constrained chiral analogues of peptide nucleic acids (PNA) based on the pyrrolidine core structure, we have recently shown that a pyrrolidinyl PNA derived from alternating 4'R-thymin-1-ylpyrrolidine-2'R-carboxylic acid and aminopyrrolidine-2R-carboxylic acid (D-Apc) residues, could bind to its complementary oligodeoxynucleotide as shown by gel electrophoresis. We have further investigated the interaction between pyrrolidinyl PNA and nucleic acids by UV and CD spectroscopy and have discovered that pyrrolidinyl PNA displays a remarkable preferential affinity for complementary DNA over RNA.

Materials and Methods

The solid support for peptide synthesis, Novasyn™ TGR resin (~0.20–0.25 mmol free $NH_2$ group/g) and Fmoc-Lys(Boc)-OPfp were obtained from Calbiochem-Novabiochem Ltd. Trifluoroacetic acid (98%) was obtained from Avocado Research Chemicals Ltd and Fluka AG. All other reagents were obtained at highest purity grade available either from Aldrich Chemical Company Ltd. or Fluka AG. and were used as received.

DMF was peptide synthesis grade obtained from Rathburn Chemicals Ltd. and used without further purification. All other solvents used for the synthesis and purification were hplc grade solvents obtained from Rathburn. Deionized water was obtained from an Elga Maxima Ultra-Pure water purification system.

Samples for reverse phase hplc analysis were dissolved in a suitable aqueous solvent and filtered through a teflon filter (0.47μ pore size, Anachem Ltd.). Hplc was performed on a Waters 990+ system with a diode array detector. A Waters μBondapak C-18 semi-preparative reverse phase hplc column (0.78×30 cm, P/N 84176) or Hypersil ODS 100×4.6 mm, 5μ particle size was used for both analysis and preparative purposes. Peak monitoring and data analysis were performed on Waters 990 software running on a NEC IBM-PC/AT compatible computer with 80286/80287 microprocessors. The samples were recovered from hplc fractions by freeze drying on a VirTis Freezemobile 5SL freeze drier.

General Protocol for Solid Phase Synthesis of PNA (Fmoc Chemistry)

Synthesis of PNA was carried out on 2.5 or 5.0 mmol scales on Novasyn TGR resin [0.20 mmol/g substitution, reloaded with Fmoc-Lys(Boc)-OH; 10–25 mg, ca. 2.5–5 μmol].

The synthesis cycle is as follows: deprotection: 20% piperidine in DMF (1.0 mL, 15 min), wash (DMF), coupling [Pfp esters S1 or S2/HOAt (1:1) in DMF, 4 eq, 1 h], wash (DMF), capping (10% $Ac_2O$/lutidine in DMF, wash (DMF). The coupling reaction was monitored by measurement of the amounts of dibenzofulvene-piperidine adduct released upon deprotection at 264 and 297 μm. After addition of the final residue was completed, the N-terminal Fmoc group was either removed by 20% piperidine in DMF or retained depending on the efficiency of the synthesis. The PNA was released from the resin by treatment with 95% trifluoroacetic acid (ca. 1 mL for 10 mg resin) at room temperature for 2–3 h with occasional agitation. After the specified period of time, the cleavage solution was evaporated to nearly dryness by a stream of nitrogen then diluted with diethyl ether (ten times the volume). The suspension was then centrifuged at 13,000 rpm for 5 min. After decanting the supernatant, the crude PNA was washed with ether and the centrifugation-wash process repeated 2–3 times. Finally the crude PNA was air dried and dissolved in 10% aqueous acetonitrile containing 0.1% trifluoroacetic acid. The crude solution was filtered and analysed or purified by reverse phase hplc. The sample elution was carried out using a gradient of water-acetonitrile containing 0.1% trifluoroacetic acid (monitoring by UV absorbance at 270 nm).

General Protocol for Removal of Fmoc Group From Purified Fmoc-ON PNA

To the freeze dried PNA (20–50 μg) was added 20% piperidine in DMF (20–50 μL) and the solution mixed by vortexing. After 20 min at room temperature, ether was then added. The precipitated peptide was isolated by centrifugation and washed a few times with ether and finally air dried. The residue was dissolved in aqueous acetonitrile and purified by reverse phase hplc.

3b: H-[D-Apc-D-Pro(cis-4-T)]$_{10}$-LysNH$_2$
calculated coupling yield: 85% (before final Fmoc-deprotection)
$t_R$=25.5 min (Fmoc-OFF); 28.9 min (Fmoc-ON)

hplc conditions:
column—Hypersil ODS 100×4.6 mm, 5μ particle size
solvents—A=0.1% TFA in MeCN, B=0.1% aqueous TFA, 10:90 A:B for 5 min then linear gradient to 90:10 A:B over a period of 30 min $M_r$ (MALDI-TOF) found 3479.3, calcd. for M.H$^+$=3479.7

Biophysical Studies—General

Poly(rA) (potassium salt, $M_r$~7×10$^6$) and poly(rU) (potassium salt, $M_r$<9×10$^5$) was obtained from Fluka AG. Poly(dA) (sodium salt, $M_r$~9.19×10$^4$) was obtained from Amersham Pharmacia Biotech. These nucleic acids were used as received without further treatment. Short oligonucleotides were synthesized on Applied Biosystems DNA synthesizer model 380B and were deprotected by treatment with concentrated aqueous ammonia at 55° C. overnight. The oligonucleotides were purified by ethanol precipitation. The concentration of oligonucleotide, nucleic acids and PNA solutions was determined from the absorbance at 257 or 260 nm. The molar extinction coefficients at 257 nm ($\epsilon_{257}$) of 10.0 and 9.7 mL.μmol$^{-1}$.cm$^{-1}$ per nucleotide were used for poly(rA) and poly(dA) respectively.[1] For shorter oligonucleotides the molar extinction coefficients at 260 nm ($\epsilon_{260}$) of 8.8 and 15.4 mL.μmol$^1$.cm$^{-1}$ were used for T and A respectively without compensation of the hyperchromicity resulting from partial stacking of the bases at room temperature.

$T_m$ Experiments $T_m$ experiments were performed on a CARY 100 UV Spectrophotometer (Varian Ltd.) equipped with a thermal melt system. The sample for $T_m$ measurement was prepared by mixing calculated amounts of stock oligonucleotide and PNA solutions together to give final concentration of nucleotides and sodium phosphate buffer (pH 7.0) and the final volumes were adjusted to 3.0 mL by addition of deionized water. The samples were transferred to a 10 mm quartz cell with teflon stopper and equilibrated at the starting temperature for at least 30 min. The OD$_{260}$ was recorded in steps from 25–90° C. (block temperature) with a temperature increment of 0.5° C./min. The results were normalized by dividing the absorbance at each temperature by the initial absorbance. Analysis of the data was performed on a PC-compatible computer using Microsoft Excel 97 (Microsoft Corp.).

Calculation of Thermodynamic Parameters[2-4]

Values of the equilibrium constant, K, were determined at each temperature using the equation $$K = \alpha(C_T/n)/[(1-\alpha)C_T]^n$$

where $C_T$ is the total strand concentration, a is fraction of single strand in the duplex state and n is the molecularity of the reaction (in this case n=2). Only points with 0.11<α<0.91 were used. Assuming a two-state transition model and ΔH is independent of the temperature, the plot of in K vs 1/T should be linear with slope=–ΔH/R and y-intercept=ΔS/R. The error was estimated to be in the range of ±10% due to the uncertainty of the baseline in the UV melting curve.

UV-Titration Experiments

The UV titration experiment was performed on a CARY 100 UV Spectrophotometer (Varian Ltd.) at 25° C. To a solution containing the PNA 3b (0.39 μM) and 10 mM sodium phosphate buffer pH 7.0 (2.0 mL) was added a 2–10 μL aliquot of a concentrated stock solution of (dA)$_{10}$ (concentration=36.7 μM sodium phosphate buffer pH 7.0. The absorbance was read against a blank (10 mM sodium phosphate) and more (dA)$_{10}$ aliquots were added until a total volume of 90 μL (corresponds to 1:4 T:A ratio) has been added. The ratio of the observed OD$_{260}$ and the calculated OD$_{260}$ were plotted against the mole ratio of T:A nucleotide and the stoichiometry was determined from the inflection point.[5]

Circular Dichroism Spectroscopy

All CD experiments were performed on a JASCO Model J-710/720 spectropolarimeter (Oxford Centre of Molecular Sciences, Oxford). The samples were prepared by mixing calculated amounts of stock oligonucleotide and PNA solutions together in a 10 mm quartz cell and the final volumes were adjusted to 2.00 mL by addition of deionized water containing an appropriate amount of sodium phosphate buffer pH 7.0 and sodium chloride to give the appropriate concentration of each component as described in the text. The spectra was measured at 20° C. from 300 to 200 nm and averaged 4 times then subtracted from a spectrum of pure water under the same conditions.

CD-Titration Experiments

To a solution containing poly(dA) (8.0 μM dA) or poly (rA) (7.7 μM A) and 10 mM sodium phosphate buffer pH 7.0 (2.0 mL) was added a 2.5 μL aliquot of a concentrated stock solution of 3b (concentration=2.0 mM dT) in 10 mM sodium phosphate buffer pH 7.0. The spectra were measured at 20° C. from 300 to 200 nm and averaged 4 times then subtracted from a spectrum of pure water under the same conditions. More 3b stocks were added until a total volume of 20 μL had been added.

REFERENCES

1. Steely, H. Jr; Gray, D. M.; Ratliff, R. L. *Nucleic Acids Res.* 1986, 14. 10071.
2. Tomac, S.; Sarkar, M.; Ratilainen, T.; Wittung, P.; Nielson, P. E.; Norden, B.; Graslund, A. *J Am. Chem. Soc.* 1996, 118, 5544.
3. Marky, L. A., Breslauer, K. J. *Biopolymers* 1987, 26, 1601
4. Puglisi, J. D., Tinoco, I. *Methods Enzymology* 1989, 180, 304
5. Cassani, C., Bollum, F. J. *Biochemistry* 1969, 8, 3928.

The homothymine decamer 3b [H-D-Apc-D-Pro(cis-4-T)]$_{10}$-LysNH$_2$ was synthesized from the corresponding pentafluorophenyl-activated monomers using Fmoc-solid phase methodology as described above. The identity of the product was confirmed by MALDI-TOF mass spectrometry (m/z found 3479.3, calcd for M.H$^+$ 3479.7).

A mixture of 3b and poly(da) at 1:1 T:A ratio (2 μM 3b, 150 mM NaCl, 100 mM Na phosphate buffer pH 7.0) showed a temperature dependence of the UV absorption at 260 mm (FIG. 2). Only a single transition was observed in the region of 20–90° C. The $T_m$ was estimated to be >85° C. although the accurate value could not be obtained since the melting was not complete even at 95° C. Under the same conditions, the mixture of 3b and (dA)$_{10}$ also gave a single transition melting curve with a slightly lower $T_m$ value (76° C.). In contrast, a 1:1 mixture of 3b and poly(rA) showed a single transition with much lower $T_m$ (32° C.). In all cases the melting was reversible on a cooling-re-heating cycle and no hysteresis was observed at the heating/cooling rate of 0.5° C./min which is indicative of fast complex formation and dissociation. No binding to poly(rU) was observed under the same conditions suggesting that the interaction is specific for AT pairing. In order to further demonstrate the specific recognition of adenine in DNA by thymine in the PNA 3b, $T_m$ of hybrids formed between 3b and (dA)$_{10}$ (perfect match), d(A$_4$TA$_5$), d(A$_3$TATA$_4$) and (dT)$_{10}$ were determined under low salt conditions (Table 2, entry 1–4). It was clearly shown that introduction of a mismatch base pair resulted in a large decrease of the T$_m$ (ΔT$_m$>20° C. per mismatch). No binding to (dT$_{10}$) was observed, as expected, thus demonstrating that the binding is indeed specific for AT pairing. The decrease in T$_m$ observed for a single mismatch is significantly greater than PNA 1a-oligodeoxynucleotide hybrid (ΔT$_m$~13° C.), and in fact, many other PNA reported.

Figure 3:
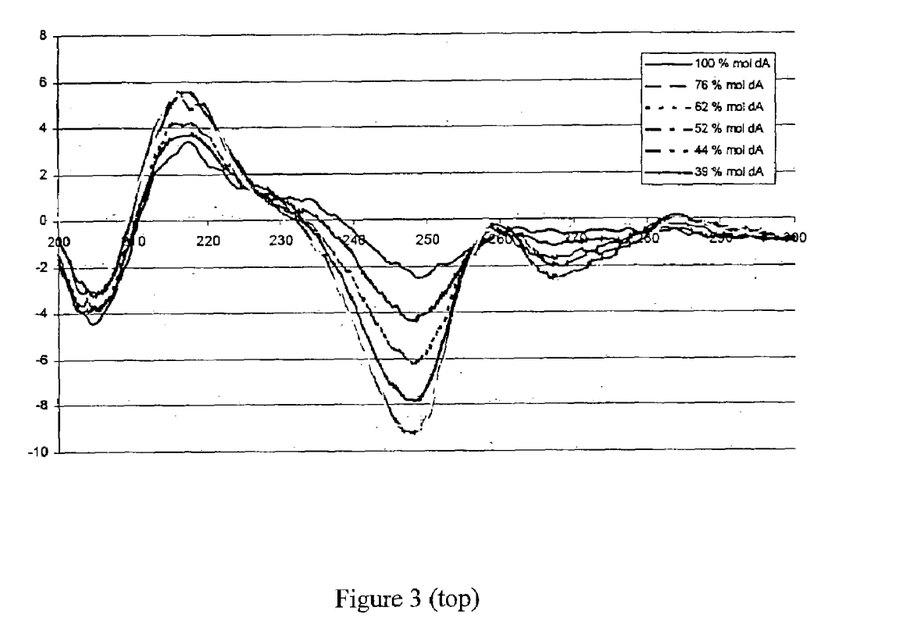
FIG. 3: Top: CD titration curve of PNA (3b) and poly (dA). Conditions: concentration of poly(dA) was constant at 8.0 μM dA, 10 mM sodium phosphate buffer, pH 7.0, 20° C. For clarity not all the CD spectra are shown, in particular, below 45% mol dA spectra are identical. Bottom: a plot between percentage mole A and the ellipticity of 3b-poly (dA) and 3b-poly(rA) hybrids.

The hybridisation properties of 3b was also studied by CD spectroscopy. The PNA 3b itself exhibited negligible CD signal in the region of 200–300 nm as compared to poly(dA) at similar concentration. Upon addition of a solution of 3b to poly (dA), a large CD signal change was observed which was not the sum of CD spectra of both components indicating the formation of a complex with a well-defined chiral conformation. By following the CD signal of the mixture at different ratios of the reactants, the 1:1 stoichiometry of the PNA:DNA hybrid was established (FIG. 3). Even at high ionic strength (1M NaCl) there was no evidence of triplex formation suggesting the 1:2 complex is structurally precluded. Addition of 3b to poly(rA) also induced a dramatic change in the CD spectrum although saturation was not observed even at a 4:1 PNA:RNA ratio. This is not surprising considering that the T$_m$ of the PNA RNA hybrid is not much above the temperature at which the study was carried out (20° C.). As a result, the stoichiometry of the hybrid formed between 3b and poly(rA) could not be determined. The CD spectrum of the 1:1 hybrid formed between 3b and poly(dA) showed negative bands (ellipticity minima) at 205, 248 and 267 nm and positive bands with maxima (ellipticity maxima) at 218, 260 and 284 nm with a low-wavelengths crossover point at 210 nm which is very similar to the B-type double helix formed between poly(dT) and poly(dA).

UV titration as well as gel electrophoresis experiments provide further supporting evidence that 3b and (DA)$_{10}$ form a 1:1 hybrid. From the specificity observed and the stoichiometry data, it is very likely that the complex is formed by Watson-Crick (A.T) base pairing. Based on the 1:1 stoichiometry and assuming an all-or-none hybridisation model, the binding enthalpy and entropy were calculated from van't Hoff plot to be −10.0 kcal and −27.2 cal.K$^{-1}$ per mole of nucleotide respectively.

In order to determine whether the tight binding of the pyrrolidinyl PNA was restricted to complementary homopolymers of DNA, two mixed sequences of PNA (3) were synthesized, H-T$_5$AT$_4$LysNH$_2$ (3e MALDI-TOF m/z found 3485.0, calc. for M 3485.5) and H-T$_3$ATAT$_4$ LysNH$_2$ (3f, MALDI-TOF m/z found 3493.6 calc. for M 3494.6) and their T$_m$ determined with complementary oligodeoxyribonucleotides assuming antiparallel binding. The data are shown in Table 3. Entries 4 and 7, show that the mixed sequence PNA bind to complementary oligonucleotides with similar T$_m$=70±1° C. and only 10° C. below that of the homopolymer PNA (3b) with dA$_{10}$. A single mismatch can, however, cause a fall in T$_m$ of 20–35° C. (entries 1–4) and a double mismatch (entry 5) prevents measurable binding at 20° C. Thus this novel class of pyrrolidinyl PNA show powerful discrimination for DNA and for matched sequences, even a single mismatch causing a large fall in T$_m$.

TABLE 3

T$_m$ of PNA H-T$_5$AT$_4$-LysNH$_2$ (3e) and H-T$_3$ATAT$_4$-LysNH$_2$ (31) with oligonucleotides

| Entry | PNA | Oligonucleotide (conditions)$^a$ | T$_m$, ° C.$^b$ (% hyperchromicity) | Note |
|---|---|---|---|---|
| 1 | 3e | d(A$_4$GA$_5$) | 36 (8) | Single mismatch |
| 2 | 3e | d(A$_4$CA$_5$) | 48 (12) | Single mismatch |
| 3 | 3e | (dA)$_{10}$ | 51 (9) | Single mismatch |
| 4 | 3e | d(A$_4$TA$_5$) | 71 (15) | Perfect match |
| 5 | 3f | (dA)$_{10}$ | <20 | Double mismatch |
| 6 | 3f | d(A$_4$TA$_5$) | 44 (15) | Single mismatch |
| 7 | 3f | d(A$_4$TATA$_3$) | 69 (18) | Perfect match |

$^a$If not otherwise indicated, the T$_m$ was measured at a ratio of PNA:DNA=1:1, concentration of PNA strand=1 μM, 10 mM sodium phosphate buffer, pH 7.0, heating rate 0.5° C./min; $^b$T$_m$ was determined from first derivative plot.

The unusual stability of the hybrid formed between pyrrolidinyl PNA and oligodeoxy ribonucleotides could at least partly be attributed to the electrostatic attraction between the positively charged hydrazine nitrogen atom on PNA to the negatively charged phosphate group of the DNA. The above proposal was supported by the fact that T$_m$ of the hybrid is sensitive to pH, being greater at lower pH (Table 2, entries 5,6). Furthermore, the T$_m$ is also dependent on ionic strength (Table 2, entries 7,8), being decreased at higher ionic strength similar to other positively-charged oligonucleotide analogues. The presence of the structurally rigid aminoproline linker with appropriate geometry is probably another factor that contributes to the strong binding properties of the PNA (3b). It is interesting to note that while PNA (3b) bearing the D-aminoproline spacer binds strongly to DNA, the corresponding PNA (3a) bearing L-aminoproline spacer showed no observable binding according to gel-binding shift assay and T$_m$ experiments.

TABLE 2

T$_m$ of PNA-nucleic acid hybrids

| Entry | PNA | Oligonucleotide (conditions)$^a$ | T$_m$, ° C.$^b$ (% hyperchromicity) |
|---|---|---|---|
| 1 | 3b | (dA)$_{10}$ | 80 (18) |
| 2 | 3b | d(A$_4$TA$_5$) | 57 (15) |
| 3 | 3b | d(A$_3$TATA$_4$) | <30 (6)$^c$ |
| 4 | 3b | (dT)$_{10}$ | — |
| 5 | 3b | (dA)$_{10}$ (pH 5.5) | 80 (18) |
| 6 | 3b | (dA)$_{10}$ (pH 8.0) | 71 (17) |
| 7 | 3b | (dA)$_{10}$ (100 mM NaCl) | 76 (17) |
| 8 | 3b | (dA)$_{10}$ (500 mM NaCl) | 74 (16) |
| 9 | 1a | (rA)$_{10}$ (100 mM NaCl) | 81 (−)$^d$ |
| 10 | 1a | (dA)$_{10}$ (100 mM NaCl) | 72 (−)$^d$ |

$^a$If not otherwise indicated, the T$_m$ was measured at a ratio of PNA:DNA=1:1, concentration of PNA strand=2 μM, 10 mM sodium phosphate buffer, pH 7.0, heating rate 0.5° C./min; $^b$T$_m$ was determined from first derivative plot; $^c$Partial melting was observed at the lowest temperature used for melting curve determination (25° C.) $^d$Data taken from Haaina et al, New J. Chem 1999 23, 833–839. The % hyperchromicity was not reported.

The different behaviour towards poly(dA) and poly(rA) of PNA 3b is perhaps the most striking feature of this β-amino acid containing PNA. The preference of binding to DNA

The invention claimed is:

1. A compound of formula:

where n is 1, or 2 to 200 in which case each recurring unit can be the same or different,

B is a protected or unprotected base capable of Watson-Crick or of Hoogsteen pairing, C is OH or OR''' where R''' is a protecting group or an activating group or a lipophilic group or an amino acid or amino amide or nucleoside,

D is H or a protecting group or a lipophilic group or an amino acyl group or nucleoside, each of R' and R'', which may be the same or different, is an alkyl or aryl group or R' and R'' together represent 2 or more chain atoms necessary to complete an unsaturated or saturated ring with X and Y, said ring being optionally substituted and optionally being fused to at least one other ring, X represents and Y represents or wherein Y' represents hydrogen or additionally, when R' and R'' do not together complete a ring, an alkyl or aryl group, and X', when R' and R'' together complete a ring, represents hydrogen or forms a bridge with another atom of the ring, or when R' and R'' do not together complete a ring, represents hydrogen or an alkyl or aryl group.

2. A compound according to claim 1 wherein R' and R'' together represent 2 to 5 chain atoms.

3. A compound according to claim 2 wherein R' and R'' together complete a 4, 5 or 6 membered nitrogen containing ring.

4. A compound according to claim 1 wherein R' and R'' together complete a saturated ring.

5. A compound according to claim 1 wherein Y represents

6. A compound according to claim 1 wherein R' and R'' together complete a pyrrolidine ring.

7. A compound according to claim 1 wherein R' and R'' complete a ring with X and Y which is fused to a 5 or 6 membered ring which is saturated or aromatic.

8. A compound according to claim 1 wherein X' forms a —$CH_2$— or —$CH_2$—$CH_2$— bridge with another carbon atom of the ring.

9. A compound according to claim 1 wherein B is a naturally occurring nucleobase which is adenine, cytosine, guanine, thymine and uracil.

10. A compound according to claim 9, wherein C is OH and B is thymine.

11. A compound according to claim 1, wherein n is 1, B is a naturally occurring nucleobase which is adenine, cytosine, guanine, thymine and uracil, R''' is an activating group, and D is H or a protecting group.

12. A compound according to claim 1, wherein n is 5–30.

13. A hybrid comprising two strands of which a first strand is a compound according to claim 1 wherein n is greater than 1 and a second strand is an oligo- or polynucleotide or nucleic acid.

14. A hybrid according to claim 13, wherein the two strands are hybridised to one another in a 1:1 molar ratio by base-specific Watson-Crick base pairing.

15. A process for preparing a compound as claimed in claim 1 which comprises:

(i) de-protecting the heterocyclic amino group of a compound of the formula

(a)

where $R^2$ is a protecting group, $R^3$ is a protecting group compatible with $R^2$, and B is a protected or unprotected heterocyclic base capable of Watson-Crick or Hoogsteen pairing (ii) de-protecting the compound of the formula:

(b)

wherein X, Y, $R^2$ and $R^3$ are as defined above, and (iii) coupling the two deprotected compounds together and optionally removing said protecting groups.

16. A process according to claim 15 wherein $R^2$ is Dpm or Pfp and $R^3$ is Boc or Fmoc.

17. A method of converting a compound as claimed in claim 1 in which n is 1 into a compound as claimed in claim 1 in which n is 2–200, comprising the steps of:
(i) providing a support carrying primary amine groups,
(ii) coupling an N-protected compound as claimed in claims 1 wherein n is 1 to the support,
(iii) removing the N-protecting group,
(iv) coupling an N-protected compound as claimed in claim 1 wherein n is 1 to the thus-derivatised support,
(v) repeating steps (iii) and (iv) one or more times, and
(vi) optionally removing the resulting peptide oligonucleotide from the support.

18. A method according to claim 17, wherein a pentafluorophenyl ester of the compound is used in step (ii) and (iii).

19. A pharmaceutical composition which comprises a compound as claimed in claim 1 and a pharmaceutically acceptable diluent or carrier.

20. A method of analysing a polynucleotide sequence comprising incubating the sequence with a probe comprising a compound according to claim 1 in which n is 2 or more under suitable hybridisation conditions, and detecting the presence or absence of any hybrid formed.

21. A method according to claim 20 wherein bases B of the probe are selected to be complementary to or to have one or more mismatches to a target sequence and wherein the hybridisation studies are carried out under conditions to allow sequence complementary to the probe to be distinguished from a sequence containing a mismatch with respect to the probe.

22. A method according to claim 20 wherein the method comprises the steps of:
incubating the polynucleotide sequence with the probe comprising a compound according to claim 1 wherein n is two or more; and
optionally washing unbound probes from the polynucleotide sequence;
wherein the method is carried out under conditions which allow a sequence complementary to the probe to be distinguished from sequence containing a mismatch sequence with respect to the probe;
and detecting any hybrid so formed.

23. A method according to claim 20 wherein the polynucleotide sequence is bound to a solid support.

24. A method according to claim 20 in which the probe is labelled.

25. A method according to claim 20 wherein two probes are provided, the base B of the probes being selected such that one of the probes is complementary to the target sequence and one of the probes has a mismatch with respect to the target sequence.

26. A method according to claim 25 wherein each of the two probes are labelled with a different label.

* * * * *